United States Patent
Dorai et al.

(10) Patent No.: US 7,888,117 B2
(45) Date of Patent: Feb. 15, 2011

(54) HUMAN OCT-2 VARIANT PEPTIDE CHAINS, NUCLEIC ACIDS, AND METHODS

(76) Inventors: Haimanti Dorai, 340 Long Ridge La., Exton, PA (US) 19341; Jin Lu, 3756 Old Post Cir., Boothwyn, PA (US) 19061

( * ) Notice: Subject to any disclaimer, the term of this patent is extended or adjusted under 35 U.S.C. 154(b) by 745 days.

(21) Appl. No.: 11/750,053

(22) Filed: May 17, 2007

(65) Prior Publication Data

US 2007/0292915 A1  Dec. 20, 2007

Related U.S. Application Data

(60) Provisional application No. 60/801,127, filed on May 17, 2006.

(51) Int. Cl.
*C12N 5/00* (2006.01)
*C07K 14/00* (2006.01)
*C07H 21/04* (2006.01)

(52) U.S. Cl. ............ 435/325; 530/350; 536/23.5; 536/23.1

(58) Field of Classification Search ............ None
See application file for complete search history.

(56) References Cited

FOREIGN PATENT DOCUMENTS

WO   2005/017121 A   2/2005

OTHER PUBLICATIONS

Jeremy M. Boss, Regulation of transcription of MHC class II genes, Current Opinion in Immunology, 9: 107-113 (1997).
Clerc, et al., "The B-cell-specific Oct-2 protein contains POU box- and homeo box-type domains," Genes Development, 2: 1570-1581 (1988).
Corcoran, et al., "Oct-2, although not required by early B-cell development, is critical for later B-cell maturation and for postnatal survival," Genes Development, 7: 570-582 (1993).
Dorai, et al., "Correlation of Heavy and Light Chain mRNA Copy Numbers to Antibody Productivity in Mouse Myelma Production Cell Lines," Hybridoma, 25(1): 1-9 (2005).
Freundlieb, et al., "A Tetracycline Controlled Activation/Repression System with Increased Potential for Gene Transfer into Mammalian Cells," The Journal of Gene Medicine, 1: 4-12 (1999).
Liu, et al., "Adjacent proline resides in the inhibitory domain of the Oct-2 transcription factor play distinct functional roles," Nucleic Acids Research, 26(10): 2464-2472 (1998).
Patrick Matthias, "Lymphoid-specific transcription mediated by the conserved octamer site: Who is doing what?" Immunology, 10: 155-163 (1998).
Müller, et al., "A cloned octamer transcription factor stimulated transcription from lymphoid-specific promoters in non-B cells," Nature, 336: 544-551 (1988).
Sáez, et al., "Analysis of Octamer-Binding Transcription /Factors Oct2 and Oct1 and their coactivator BOB.1/OBF.1 in Lymphomas," Modern Pathology, 15(3): 211-220 (2002).
Strubin, et al. "OBF-1, a novel B-cell specific co-activator that stimulates immunoglobulin promoter activity through association with Octamer binding proteins," Cell, 80: 497-506 (1995).
Suzuki, et al., "Mouse Oct-1 contains a composite homeodomain of human Oct-1 and Oct-2," nucleic Acids Research 21(2): 245-252 (1993).
Wirth, et al., "Multiple Oct2 isoforms are generated by alternative splicing," Nucleic Acids Research, 19(1): 43-51 (1991).
Zhang, et al., "Synthetic Zinc Finger Transcription Factor Action at an Endogenous Chromosomal Site," The Journal of Biological Chemistry, 275(43): 33850-33860 (2000).
Zwilling, et al., "The POU domains of the Oct1 and Oct2 transcription factors mediate specific interaction with TBP," Nucleic Acids Research, 22(9): 1655-1662 (1994).
PCT International Search Report dated Apr. 15, 2008.
Supplemental European Search Report dated Oct. 16, 2009.

*Primary Examiner*—Nashaat T Nashed
(74) *Attorney, Agent, or Firm*—Kirk Baumeister

(57) ABSTRACT

*Homo sapiens* OCT-2 variant peptide chains are disclosed. Polynucleotides encoding these peptide chains, cells comprising these polynucleotides, and methods of using the forgoing are also disclosed.

9 Claims, 4 Drawing Sheets

Fig. 2

```
1 NP_002689    MVHSSMGAPEIRMSK PLEAEKQGLDSPSEH TDTERNGPDTNHQNP QNKTS PFSVSPTGPS TKIKAEDPSGDSAPA APLPPQPAQPHLPQA    90
2 Clone#19     MVHSSMGAPEIRMSK PLEAEKQGLDSPSEH TDTERNGPDTNHQNP QNKTS PFSVSPTGPS TKIKAEDPSGDSAPA APLPPQPAQPHLPQA    90
3 Clone#38     MVHSSMGAPEIRMSK PLEAEKQGLDSPSEH TDTERNGPDTNHQNP QNKTS PFSVSPTGPS TKIKAEDPSGDSAPA APLPPQPAQPHLPQA    90
4 M36653       MVHSSMGAPEIRMSK PLEAEKQGLDSPSEH TDTERNGPDTNHQNP QNKTS PFSVSPTGPS TKIKAEDPSGDSAPA APLPPQPAQPHLPQA    90
                      1              15 16             30 31              45 46             60 61             75 76             90

1 NP_002689    QLMLTGSQLAGDIQQ LLQLQQLVLVPGHHL QPPAQFLLPQAQQSQ PGLLPTPNLFQLPQQ TQGALLTSQPRAGLP ----------------   165
2 Clone#19     QLMLTGSQLAGDIQQ LLQLQQLVLVPGHHL QPPAQFLLPQAQQSQ PGLLPTPNLFQLPQQ TQGALLTSQPRAGLP ----------------   165
3 Clone#38     QLMLTGSQLAGDIQQ LLQLQQLVLVSGHHL QPPAQFLLPQAQQSQ PGLLPTPNLFQLPQQ TQGALLTSQPRAGLP ----------------   165
4 M36653       QLMLTGSQLAGDIQQ LLQLQQLVLVPGHHL QPPAQFLLPQAQQSQ PGLLPTPNLFQLPQQ TQGALLTSQPRAGLP QAVTRPTLPDPHLS    180
                     91             105 106            120 121            135 136            150 151            165 166            180

1 NP_002689    -TQPPKCLEPPSHPE EPSDLEELEQFARTF KQRRIKLGFTQGDVG LAMGKLYGNDFSQTI ISRFEALNLSFKNMC KLKPLIEKWINDAET   254
2 Clone#19     -TQPPKCLEPPSHPE EPSDLEELEQFARTF KQRRIKLGFTQGDVG LAMGKLYGNDFSQTI ISRFEALNLSFKNMC KLKPLIEKWINDAET   254
3 Clone#38     -TQPPKCLEPPSHPE EPSDLEELEQFARTF KQRRIKLGFTQGDVG LAMGKLYGNDFSQTI ISRFEALNLSFKNMC KLKPLIEKWINDAET   254
4 M36653       HPQPPKCLEPPSHPE EPSDLEELEQFARTF KQRRIKLGFTQGDVG LAMGKLYGNDFSQTI ISRFEALNLSFKNMC KLKPLIEKWINDAET   270
                    181             195 196            210 211            225 226            240 241            255 256            270

1 NP_002689    MSVDSSLPSPNQLSS PSLGFDGLFGRRRKK RTSIETNVRFALEKS FLANQKPTSEEILLI AEQLHMEKEVIRVWF CNRRQKEKRINPCSA   344
2 Clone#19     MSVDSSLPSPNQLSS PSLGFDGLFGRRRKK RTSIETNVRFALEKS FLANQKPTSEEILLI AEQLHMEKEVIRVWF CNRRQKEKRINPCSA   344
3 Clone#38     MSVDSSLPSPNQLSS PSLGFDGLFGRRRKK RTSIETNVRFALEKS FLANQKPTSEEILLI AEQLHMEKEVIRVWF CNRRQKEKRINPCSA   344
4 M36653       MSVDSSLPSPNQLSS PSLGFDGLFGRRRKK RTSIETNVRFALEKS FLANQKPTSEEILLI AEQLHMEKEVIRVWF CNRRQKEKRINPCSA   360
                    271             285 286            300 301            315 316            330 331            345 346            360

1 NP_002689    APMLPSPGKPASYSP HMVTPQGGAGTLPLS QASSSLSTTVTTLSS AVGTLHPSRTAGGGG GGGGAAPPLNSIPSV TPPPPATTNSTNPSP   434
2 Clone#19     APMLPSPGKPASYSP HMVTPQGGAGTLPLS QASSSLSTTVTTLSS AVGTLHPSRTAGGGG GGGGAAPPLNSIPSV TPPPPATTNSTNPSP   434
3 Clone#38     APMLPSPGKPASYSP HMVTPQGGAGTLPLS QASSSLSTTVTTLSS AVGTLHPSRTAGGGG GGGGAAPPLNSIPSV TPPPPATTNSTNPSP   434
4 M36653       APMLPSPGKPASYSP HMVTPQGGAGTLPLS QASSSLSTTVTTLSS AVGTLHPSRTAGGGG GGGGAAPPLNSIPSV TPPPPATTNSTNPSP   450
                    361             375 376            390 391            405 406            420 421            435 436            450

1 NP_002689    QGSHSAIGLSGLNPS TGPGLWNFAPYQP   463
2 Clone#19     QGSHSAIGLSGLNPS TG-----------   451
3 Clone#38     QGSHSAIGLSGLNPS TG-----------   451
4 M36653       QGSHSAIGLSGLNPS TG-----------   467
                    451             465 466            480
```

SEQUENCE LISTING

```
<160> NUMBER OF SEQ ID NOS: 19

<210> SEQ ID NO 1
<211> LENGTH: 1389
<212> TYPE: DNA
<213> ORGANISM: Homo sapiens

<400> SEQUENCE: 1
atggttcact ccagcatggg ggctccagaa ataagaatgt ctaagcccct ggaggccgag      60
aagcaaggtc tggactcccc atcagagcac acagacaccg aaagaaatgg accagacact     120
aatcatcaga accccaaaa taagacctcc ccattctccg tgtccccaac tggccccagt     180
acaaagatca aggctgaaga ccccagtggc gattcagccc cagcagcacc cctgccccct     240
cagccggccc agcctcatct gccccaggcc caactcatgt tgacgggcag ccagctagct     300
ggggacatac agcagctcct ccagctccag cagctggtgc ttgtgccagg ccaccacctc     360
cagccacctg ctcagttcct gctaccgcag gcccagcaga gccagccagg cctgctaccg     420
acaccaaatc tattccagct acctcagcaa acccaggag ctcttctgac ctcccagccc     480
cgggccgggc ttcccacaca gccccccaaa tgcttggagc caccatccca ccccgaggag     540
cccagtgatc tggaggagct ggagcaattc gcccgcacct tcaagcaacg ccgcatcaag     600
ctgggcttca cgcagggtga tgtgggcctg gccatgggca agctctacgg caacgacttc     660
agccagacga ccatttcccg cttcgaggcc ctcaacctga gcttcaagaa catgtgcaaa     720
ctcaagcccc tcctggagaa gtggctcaac gatgcagaga ctatgtctgt ggactcaagc     780
ctgcccagcc ccaaccagct gagcagcccc agcctgggtt cgacggcct gcccggccgg     840 agacgcaaga agaggaccag catcgagaca aacgtccgct tcgccttaga gaagagtttt     900
ctagcgaacc agaagcctac ctcagaggag atcctgctga tcgccgagca gctgcacatg     960
gagaaggaag tgatccgcgt ctggttctgc aaccggcgcc agaaggagaa acgcatcaac    1020
ccctgcagtg cggcccccat gctgccagc ccagggaagc cggccagcta cagcccccat    1080
atggtcacac cccaagggggg cgcggggacc ttaccgttgt cccaagcttc cagcagtctg    1140
agcacaacag ttactacctt atcctcagct gtggggacgc tccaccccag ccggacagct    1200
ggagggggtg gggcgggg cgggctgcg ccccccctca attccatccc ctctgtcact    1260
cccccacccc cggccaccac caacagcaca aaccccagcc ctcaaggcag ccactcggct    1320
atcggcttgt caggcctgaa cccagcacg ggccctggcc tctggtggaa ccctgccct    1380 taccagcct                                                           1389

<210> SEQ ID NO 2
<211> LENGTH: 463
<212> TYPE: PRT
<213> ORGANISM: Homo sapiens

<400> SEQUENCE: 2
```

```
Met Val His Ser Ser Met Gly Ala Pro Glu Ile Arg Met Ser Lys Pro
1               5                   10                  15

Leu Glu Ala Glu Lys Gln Gly Leu Asp Ser Pro Ser Glu His Thr Asp
            20                  25                  30

Thr Glu Arg Asn Gly Pro Asp Thr Asn His Gln Asn Pro Gln Asn Lys
        35                  40                  45

Thr Ser Pro Phe Ser Val Ser Pro Thr Gly Pro Ser Thr Lys Ile Lys
    50                  55                  60

Ala Glu Asp Pro Ser Gly Asp Ser Ala Pro Ala Pro Leu Pro Pro
65                  70                  75                  80

Gln Pro Ala Gln Pro His Leu Pro Gln Ala Gln Leu Met Leu Thr Gly
                85                  90                  95

Ser Gln Leu Ala Gly Asp Ile Gln Gln Leu Leu Gln Leu Gln Gln Leu
            100                 105                 110

Val Leu Val Pro Gly His His Leu Gln Pro Pro Ala Gln Phe Leu Leu
            115                 120                 125

Pro Gln Ala Gln Gln Ser Gln Pro Gly Leu Leu Pro Thr Pro Asn Leu
130                 135                 140

Phe Gln Leu Pro Gln Gln Thr Gln Gly Ala Leu Leu Thr Ser Gln Pro
145                 150                 155                 160

Arg Ala Gly Leu Pro Thr Gln Pro Pro Lys Cys Leu Glu Pro Pro Ser
            165                 170                 175

His Pro Glu Glu Pro Ser Asp Leu Glu Glu Leu Glu Gln Phe Ala Arg
        180                 185                 190

Thr Phe Lys Gln Arg Arg Ile Lys Leu Gly Phe Thr Gln Gly Asp Val
    195                 200                 205

Gly Leu Ala Met Gly Lys Leu Tyr Gly Asn Asp Phe Ser Gln Thr Thr
210                 215                 220

Ile Ser Arg Phe Glu Ala Leu Asn Leu Ser Phe Lys Asn Met Cys Lys
225                 230                 235                 240

Leu Lys Pro Leu Leu Glu Lys Trp Leu Asn Asp Ala Glu Thr Met Ser
            245                 250                 255

Val Asp Ser Ser Leu Pro Ser Pro Asn Gln Leu Ser Ser Pro Ser Leu
            260                 265                 270

Gly Phe Asp Gly Leu Pro Gly Arg Arg Arg Lys Lys Arg Thr Ser Ile
            275                 280                 285

Glu Thr Asn Val Arg Phe Ala Leu Glu Lys Ser Phe Leu Ala Asn Gln
        290                 295                 300

Lys Pro Thr Ser Glu Glu Ile Leu Leu Ile Ala Glu Gln Leu His Met
305                 310                 315                 320

Glu Lys Glu Val Ile Arg Val Trp Phe Cys Asn Arg Arg Gln Lys Glu
            325                 330                 335

Lys Arg Ile Asn Pro Cys Ser Ala Ala Pro Met Leu Pro Ser Pro Gly
            340                 345                 350

Lys Pro Ala Ser Tyr Ser Pro His Met Val Thr Pro Gln Gly Gly Ala
            355                 360                 365

Gly Thr Leu Pro Leu Ser Gln Ala Ser Ser Ser Leu Ser Thr Thr Val
            370                 375                 380

Thr Thr Leu Ser Ser Ala Val Gly Thr Leu His Pro Ser Arg Thr Ala
385                 390                 395                 400

Gly Gly Gly Gly Gly Gly Gly Ala Ala Pro Pro Leu Asn Ser Ile
            405                 410                 415
```

-continued

```
Pro Ser Val Thr Pro Pro Pro Ala Thr Thr Asn Ser Thr Asn Pro
        420                 425                 430

Ser Pro Gln Gly Ser His Ser Ala Ile Gly Leu Ser Gly Leu Asn Pro
        435                 440                 445

Ser Thr Gly Pro Gly Leu Trp Trp Asn Pro Ala Pro Tyr Gln Pro
    450                 455                 460

<210> SEQ ID NO 3
<211> LENGTH: 1353
<212> TYPE: DNA
<213> ORGANISM: Homo sapiens

<400> SEQUENCE: 3
atggttcact ccagcatggg ggctccagaa ataagaatgt ctaagcccct ggaggccgag      60
aagcaaggtc tggactcccc atcagagcac acagacaccg aaagaaatgg accagacact     120
aatcatcaga ccccaaaa taagacctcc ccattctccg tgtccccaac tggccccagt      180
acaaagatca aggctgaaga ccccagtggc gattcagccc cagcagcacc cctgccccct     240
cagccggccc agcctcatct gccccaggcc caactcatgt tgacgggcag ccagctagct     300
ggggacatac agcagctcct ccagctccag cagctggtgc ttgtgccagg ccaccacctc     360
cagccacctg ctcagttcct gctaccgcag gcccagcaga gccagccagg cctgctaccg     420
acaccaaatc tattccagct acctcagcaa cccaggggag ctcttctgac ctcccagccc     480
cgggccgggc ttcccacaca gcccccaaa tgcttggagc caccatccca ccccgaggag     540
cccagtgatc tggaggagct ggagcaattc gcccgcacct tcaagcaacg ccgcatcaag     600
ctgggcttca gcagggtga tgtgggcctg gccatgggca agctctacgg caacgacttc     660
agtcagacga ccatttcccg cttcgaggcc ctcaacctga gcttcaagaa catgtgcaaa     720
ctcaagcccc tcctggagaa gtggctcaac gatgcagaga ctatgtctgt ggactcaagc     780
ctgcccagcc caaccagct gagcagcccc agcctgggtt cgacggcct gccggccgg     840 agacgcaaga gaggaccag catcgagaca acgtccgct cgccttaga aagagttt     900 ctagcgaacc agaagcctac ctcagaggag atcctgctga tcgccgagca gctgcgcatg     960
gagaaggaag tgatccgcgt ctggttctgc aaccggcgcc agaaggagaa acgcatcaac    1020
ccctgcagtg cggcccccat gctgcccagc caggggaagc cggccagcta cagccccat    1080 atggtcacac cccaaggggg gcgcgggacc ttaccgttgt cccaagcttc agcagtctg    1140 agcacaaacag ttactacctt atcctcagct gtggggacgc tccaccccag ccggacagct    1200 ggaggggtg ggggcggggg cggggctgcg ccccccctca attccatccc ctctgtcact    1260
cccccacccc cggccaccac caacagcaca aaccccagcc ctcaaggcag ccactcggct    1320
atcggcttgt caggcctgaa ccccagcacg ggg                                 1353

<210> SEQ ID NO 4
<211> LENGTH: 451
<212> TYPE: PRT
<213> ORGANISM: Homo sapiens

<400> SEQUENCE: 4

Met Val His Ser Ser Met Gly Ala Pro Glu Ile Arg Met Ser Lys Pro
1               5                   10                  15

Leu Glu Ala Glu Lys Gln Gly Leu Asp Ser Pro Ser Glu His Thr Asp
            20                  25                  30

Thr Glu Arg Asn Gly Pro Asp Thr Asn His Gln Asn Pro Gln Asn Lys
        35                  40                  45
```

```
Thr Ser Pro Phe Ser Val Ser Pro Thr Gly Pro Ser Thr Lys Ile Lys
 50                  55                  60

Ala Glu Asp Pro Ser Gly Asp Ser Ala Pro Ala Pro Leu Pro Pro
65                  70                  75                  80

Gln Pro Ala Gln Pro His Leu Pro Gln Ala Gln Leu Met Leu Thr Gly
                85                  90                  95

Ser Gln Leu Ala Gly Asp Ile Gln Gln Leu Leu Gln Leu Gln Gln Leu
            100                 105                 110

Val Leu Val Pro Gly His His Leu Gln Pro Pro Ala Gln Phe Leu Leu
        115                 120                 125

Pro Gln Ala Gln Gln Ser Gln Pro Gly Leu Leu Pro Thr Pro Asn Leu
130                 135                 140

Phe Gln Leu Pro Gln Gln Thr Gln Gly Ala Leu Leu Thr Ser Gln Pro
145                 150                 155                 160

Arg Ala Gly Leu Pro Thr Gln Pro Pro Lys Cys Leu Glu Pro Pro Ser
                165                 170                 175

His Pro Glu Glu Pro Ser Asp Leu Glu Glu Leu Glu Gln Phe Ala Arg
            180                 185                 190

Thr Phe Lys Gln Arg Arg Ile Lys Leu Gly Phe Thr Gln Gly Asp Val
        195                 200                 205

Gly Leu Ala Met Gly Lys Leu Tyr Gly Asn Asp Phe Ser Gln Thr Thr
    210                 215                 220

Ile Ser Arg Phe Glu Ala Leu Asn Leu Ser Phe Lys Asn Met Cys Lys
225                 230                 235                 240

Leu Lys Pro Leu Leu Glu Lys Trp Leu Asn Asp Ala Glu Thr Met Ser
                245                 250                 255

Val Asp Ser Ser Leu Pro Ser Pro Asn Gln Leu Ser Ser Pro Ser Leu
            260                 265                 270

Gly Phe Asp Gly Leu Pro Gly Arg Arg Arg Lys Lys Arg Thr Ser Ile
        275                 280                 285

Glu Thr Asn Val Arg Phe Ala Leu Glu Lys Ser Phe Leu Ala Asn Gln
    290                 295                 300

Lys Pro Thr Ser Glu Glu Ile Leu Leu Ile Ala Glu Gln Leu Arg Met
305                 310                 315                 320

Glu Lys Glu Val Ile Arg Val Trp Phe Cys Asn Arg Arg Gln Lys Glu
                325                 330                 335

Lys Arg Ile Asn Pro Cys Ser Ala Ala Pro Met Leu Pro Ser Pro Gly
            340                 345                 350

Lys Pro Ala Ser Tyr Ser Pro His Met Val Thr Pro Gln Gly Gly Ala
        355                 360                 365

Gly Thr Leu Pro Leu Ser Gln Ala Ser Ser Ser Leu Ser Thr Thr Val
    370                 375                 380

Thr Thr Leu Ser Ser Ala Val Gly Thr Leu His Pro Ser Arg Thr Ala
385                 390                 395                 400

Gly Gly Gly Gly Gly Gly Gly Gly Ala Ala Pro Pro Leu Asn Ser Ile
                405                 410                 415

Pro Ser Val Thr Pro Pro Pro Ala Thr Thr Asn Ser Thr Asn Pro
            420                 425                 430

Ser Pro Gln Gly Ser His Ser Ala Ile Gly Leu Ser Gly Leu Asn Pro
        435                 440                 445

Ser Thr Gly
    450
```

<210> SEQ ID NO 5
<211> LENGTH: 1353
<212> TYPE: DNA
<213> ORGANISM: Homo sapiens

<400> SEQUENCE: 5

```
atggttcact ccagcatggg ggctccagaa ataagaatgt ctaagcccct ggaggccgag    60
aagcaaggtc tggactcccc atcagagcac acagacaccg aaagaaatgg accagacact   120
aatcatcaga accccccaaaa taagacctcc ccattctccg tgtccccaac tggccccagt   180
acaaagatca aggctgaaga ccccagtggc gattcagccc cagcagcacc cctgccccct   240
cagccggccc agcctcatct gccccaggcc caactcatgt tgacgggcag ccagctagct   300
ggggacatac agcagctcct ccagctccag cagctggtgc ttgtgtcagg ccaccacctc   360
cagccacctg ctcagttcct gctaccgcag gcccagcaga gccagccagg cctgctaccg   420
acaccaaatc tattccagct acctcagcaa cccaggggag ctcttctgac ctcccagccc   480
cgggccgggc ttcccacaca gccccccaaa tgcttggagc accatcccca ccccgaggag   540
cccagtgatc tggaggagct ggagcaattc gcccgcacct tcaagcaacg ccgcatcaag   600
ctgggcttca cgcagggtga tgtgggcctg ccatgggca agctctacgg caacgacttc   660
agtcagacga ccatttcccg cttcgaggcc tcaacctga gcttcaagaa catgtgcaaa   720
ctcaagcccc tcctggagaa gtggctcaac gatgcagaga ctatgtctgt ggactcaagc   780
ctgcccagcc ccaaccagct gagcagcccc agcctgggtt cgacggcct gcccggccgg   840
agacgcaaga agaggaccag catcgagaca aacgtccgct tcgccttaga gaagagtttt   900
ctagcgaacc agaagcctac ctcagaggag atcctgctga tcgccgagca gctgcgcatg   960
gagaaggaag tgatccgcgt ctggttctgc aaccggcgcc agaaggagaa acgcatcaac  1020
ccctgcagtg cggccccat gctgcccagc ccagggaagc cggccagcta cagcccccat  1080
atggtcacac cccaaggggg cgcggggacc ttaccgttgt cccaagcttc cagcagtctg  1140
agcacaacag ttactacctt atcctcagct gtggggacgc tccacccag ccggacagct  1200
ggaggggtg ggggcggggg cggggctgcg ccccccctca attccatccc ctctgtcact  1260
ccccacccc cggccaccac caacagcaca aaccccagcc ctcaaggcag ccactcggct  1320
atcggcttgt caggcctgaa ccccagcacg ggg                                1353
```

<210> SEQ ID NO 6
<211> LENGTH: 451
<212> TYPE: PRT
<213> ORGANISM: Homo sapiens

<400> SEQUENCE: 6

```
Met Val His Ser Ser Met Gly Ala Pro Glu Ile Arg Met Ser Lys Pro
1               5                   10                  15

Leu Glu Ala Glu Lys Gln Gly Leu Asp Ser Pro Ser Glu His Thr Asp
            20                  25                  30

Thr Glu Arg Asn Gly Pro Asp Thr Asn His Gln Asn Pro Gln Asn Lys
        35                  40                  45

Thr Ser Pro Phe Ser Val Ser Pro Thr Gly Pro Ser Thr Lys Ile Lys
    50                  55                  60

Ala Glu Asp Pro Ser Gly Asp Ser Ala Pro Ala Ala Pro Leu Pro Pro
65                  70                  75                  80

Gln Pro Ala Gln Pro His Leu Pro Gln Ala Gln Leu Met Leu Thr Gly
                85                  90                  95
```

Ser Gln Leu Ala Gly Asp Ile Gln Gln Leu Leu Gln Leu Gln Gln Leu
         100                 105                 110

Val Leu Val Ser Gly His His Leu Gln Pro Pro Ala Gln Phe Leu Leu
     115                 120                 125

Pro Gln Ala Gln Gln Ser Gln Pro Gly Leu Leu Pro Thr Pro Asn Leu
 130                 135                 140

Phe Gln Leu Pro Gln Gln Thr Gln Gly Ala Leu Leu Thr Ser Gln Pro
145                 150                 155                 160

Arg Ala Gly Leu Pro Thr Gln Pro Pro Lys Cys Leu Glu Pro Pro Ser
                 165                 170                 175

His Pro Glu Glu Pro Ser Asp Leu Glu Glu Leu Glu Gln Phe Ala Arg
             180                 185                 190

Thr Phe Lys Gln Arg Arg Ile Lys Leu Gly Phe Thr Gln Gly Asp Val
         195                 200                 205

Gly Leu Ala Met Gly Lys Leu Tyr Gly Asn Asp Phe Ser Gln Thr Thr
     210                 215                 220

Ile Ser Arg Phe Glu Ala Leu Asn Leu Ser Phe Lys Asn Met Cys Lys
225                 230                 235                 240

Leu Lys Pro Leu Leu Glu Lys Trp Leu Asn Asp Ala Glu Thr Met Ser
                 245                 250                 255

Val Asp Ser Ser Leu Pro Ser Pro Asn Gln Leu Ser Ser Pro Ser Leu
             260                 265                 270

Gly Phe Asp Gly Leu Pro Gly Arg Arg Arg Lys Lys Arg Thr Ser Ile
         275                 280                 285

Glu Thr Asn Val Arg Phe Ala Leu Glu Lys Ser Phe Leu Ala Asn Gln
     290                 295                 300

Lys Pro Thr Ser Glu Glu Ile Leu Leu Ile Ala Glu Gln Leu Arg Met
305                 310                 315                 320

Glu Lys Glu Val Ile Arg Val Trp Phe Cys Asn Arg Arg Gln Lys Glu
                 325                 330                 335

Lys Arg Ile Asn Pro Cys Ser Ala Ala Pro Met Leu Pro Ser Pro Gly
             340                 345                 350

Lys Pro Ala Ser Tyr Ser Pro His Met Val Thr Pro Gln Gly Gly Ala
         355                 360                 365

Gly Thr Leu Pro Leu Ser Gln Ala Ser Ser Ser Leu Ser Thr Thr Val
     370                 375                 380

Thr Thr Leu Ser Ser Ala Val Gly Thr Leu His Pro Ser Arg Thr Ala
385                 390                 395                 400

Gly Gly Gly Gly Gly Gly Gly Gly Ala Ala Pro Pro Leu Asn Ser Ile
                 405                 410                 415

Pro Ser Val Thr Pro Pro Pro Ala Thr Thr Asn Ser Thr Asn Pro
             420                 425                 430

Ser Pro Gln Gly Ser His Ser Ala Ile Gly Leu Ser Gly Leu Asn Pro
         435                 440                 445

Ser Thr Gly
    450

<210> SEQ ID NO 7
<211> LENGTH: 768
<212> TYPE: DNA
<213> ORGANISM: Homo sapiens

<400> SEQUENCE: 7
atgctctggc aaaaacccac agctccggag caagccccag ccccggcccg gccataccag        60

-continued

```
ggcgtccgtg tgaaggagcc agtgaaggaa ctgctgagga ggaagcgagg ccacgccagc      120 agtgggcag cacctgcacc tacggcggtg gtgctgcccc atcagcccct ggcgacctac       180
accacagtgg gtccttcctg cctggacatg gaaggttctg tgtctgcagt gacagaggag      240
gctgccctgt gtgccggctg gctctcccag cccaccccgg ccaccctgca gcccctggcc     300
ccatggacac cttacaccga gtatgtgccc catgaagctg tcagctgccc ctactcagct     360
gacatgtatg tgcagcccgt gtgccccagc tacacggtgg tggggccctc ctcagtgttg     420
gcctatgcct ctccgccact catcaccaat gtcacgacaa gaagctccgc cacgcccgca     480
gtggggcccc cgctggaggg cccagagcac caggcacccc tcacctattt cccgtggcct     540
cagccccttt ccacactacc cacctccacc ctgcagtacc ggcctccggc cccagcccta     600
cctgggcccc agtttgtcca gctccccatc tctatcccag agccagtcct tcaggacatg     660
gaagacccca gaagagccgc cagctcgttg accatcgaca gctgctttt ggaggaagag      720 gatagcgacg cctatgcgct taaccacact ctctctgtgg aaggcttt                  768
```

<210> SEQ ID NO 8
<211> LENGTH: 256
<212> TYPE: PRT
<213> ORGANISM: Homo sapiens

<400> SEQUENCE: 8

```
Met Leu Trp Gln Lys Pro Thr Ala Pro Glu Gln Ala Pro Ala Pro Ala
1               5                   10                  15

Arg Pro Tyr Gln Gly Val Arg Val Lys Glu Pro Val Lys Glu Leu Leu
            20                  25                  30

Arg Arg Lys Arg Gly His Ala Ser Ser Gly Ala Ala Pro Ala Pro Thr
        35                  40                  45

Ala Val Val Leu Pro His Gln Pro Leu Ala Thr Tyr Thr Thr Val Gly
    50                  55                  60

Pro Ser Cys Leu Asp Met Glu Gly Ser Val Ser Ala Val Thr Glu Glu
65                  70                  75                  80

Ala Ala Leu Cys Ala Gly Trp Leu Ser Gln Pro Thr Pro Ala Thr Leu
                85                  90                  95

Gln Pro Leu Ala Pro Trp Thr Pro Tyr Thr Glu Tyr Val Pro His Glu
            100                 105                 110

Ala Val Ser Cys Pro Tyr Ser Ala Asp Met Tyr Val Gln Pro Val Cys
        115                 120                 125

Pro Ser Tyr Thr Val Val Gly Pro Ser Ser Val Leu Ala Tyr Ala Ser
    130                 135                 140

Pro Pro Leu Ile Thr Asn Val Thr Thr Arg Ser Ser Ala Thr Pro Ala
145                 150                 155                 160

Val Gly Pro Pro Leu Glu Gly Pro Glu His Gln Ala Pro Leu Thr Tyr
                165                 170                 175

Phe Pro Trp Pro Gln Pro Leu Ser Thr Leu Pro Thr Ser Thr Leu Gln
            180                 185                 190

Tyr Arg Pro Pro Ala Pro Ala Leu Pro Gly Pro Gln Phe Val Gln Leu
        195                 200                 205

Pro Ile Ser Ile Pro Glu Pro Val Leu Gln Asp Met Glu Asp Pro Arg
    210                 215                 220

Arg Ala Ala Ser Ser Leu Thr Ile Asp Lys Leu Leu Leu Glu Glu Glu
225                 230                 235                 240

Asp Ser Asp Ala Tyr Ala Leu Asn His Thr Leu Ser Val Glu Gly Phe
```

<210> SEQ ID NO 9
<211> LENGTH: 768
<212> TYPE: DNA
<213> ORGANISM: Mus musculus

<400> SEQUENCE: 9

```
atgctctggc aaaaatccac agctccagag caagctcctg ccccaccaag gccataccag      60
ggtgttcgag tcaaggagcc agtgaaggag ctactgagaa gaaagcgtgg ccataccagc     120
gttggggcag ctgggccacc gaccgcggtg gtactgcccc accagcccct ggccacctac     180
agcactgtgg gtccttcctg ccttgacatg gaggtttctg cttccacagt gacagaggag     240
ggaacattat gtgctggctg gctctcccaa cctgccccgg ccactcttca gccattggct     300
ccatggacac cctacacgga gtatgtgtcc catgaagctg tcagctgccc ctactccact     360
gacatgtacg tgcagcctgt gtgccccagc tacacagtgg tgggaccctc ctcggtgttg     420
acctatgctt ctccaccact catcactaat gtcacgccaa gaagcactgc tacacccgcg     480
gtggggcccc agctggaggg tcccgagcac caggcgcccc tcacttattt cccgtggcct     540
cagccccttt ccacactgcc cacctccagc ctgcagtatc aacctcctgc cccaaccctg     600
tctgggcccc agtttgtcca gctccccatc tctatcccag agccagtcct tcaggacatg     660
gatgacccca gaagggccat cagctccctg accattgaca agctgcttct ggaggaagag     720
gaaagcaaca cgtacgagct caaccacacc ctctccgtgg agggcttt                  768
```

<210> SEQ ID NO 10
<211> LENGTH: 256
<212> TYPE: PRT
<213> ORGANISM: Mus musculus

<400> SEQUENCE: 10

```
Met Leu Trp Gln Lys Ser Thr Ala Pro Glu Gln Ala Pro Ala Pro Pro
1               5                   10                  15

Arg Pro Tyr Gln Gly Val Arg Val Lys Glu Pro Val Lys Glu Leu Leu
            20                  25                  30

Arg Arg Lys Arg Gly His Thr Ser Val Gly Ala Ala Gly Pro Pro Thr
        35                  40                  45

Ala Val Val Leu Pro His Gln Pro Leu Ala Thr Tyr Ser Thr Val Gly
    50                  55                  60

Pro Ser Cys Leu Asp Met Glu Val Ser Ala Ser Thr Val Thr Glu Glu
65                  70                  75                  80

Gly Thr Leu Cys Ala Gly Trp Leu Ser Gln Pro Ala Pro Ala Thr Leu
                85                  90                  95

Gln Pro Leu Ala Pro Trp Thr Pro Tyr Thr Glu Tyr Val Ser His Glu
            100                 105                 110

Ala Val Ser Cys Pro Tyr Ser Thr Asp Met Tyr Val Gln Pro Val Cys
        115                 120                 125

Pro Ser Tyr Thr Val Val Gly Pro Ser Ser Val Leu Thr Tyr Ala Ser
    130                 135                 140

Pro Pro Leu Ile Thr Asn Val Thr Pro Arg Ser Thr Ala Thr Pro Ala
145                 150                 155                 160

Val Gly Pro Gln Leu Glu Gly Pro Glu His Gln Ala Pro Leu Thr Tyr
                165                 170                 175

Phe Pro Trp Pro Gln Pro Leu Ser Thr Leu Pro Thr Ser Ser Leu Gln
            180                 185                 190
```

Tyr Gln Pro Pro Ala Pro Thr Leu Ser Gly Pro Gln Phe Val Gln Leu
            195                 200                 205

Pro Ile Ser Ile Pro Glu Pro Val Leu Gln Asp Met Asp Asp Pro Arg
        210                 215                 220

Arg Ala Ile Ser Ser Leu Thr Ile Asp Lys Leu Leu Leu Glu Glu Glu
225                 230                 235                 240

Glu Ser Asn Thr Tyr Glu Leu Asn His Thr Leu Ser Val Glu Gly Phe
                245                 250                 255

<210> SEQ ID NO 11
<211> LENGTH: 17
<212> TYPE: DNA
<213> ORGANISM: Artificial Sequence
<220> FEATURE:
<223> OTHER INFORMATION: Forward primer for cloning nucleic acids
      encoding Homo sapiens OCT-2 variant peptide chains.

<400> SEQUENCE: 11
ggcagcatgg ttcactc                                                    17

<210> SEQ ID NO 12
<211> LENGTH: 16
<212> TYPE: DNA
<213> ORGANISM: Artificial Sequence
<220> FEATURE:
<223> OTHER INFORMATION: Reverse primer for cloning nucleic acids
      encoding Homo sapiens OCT-2 variant peptide chains.

<400> SEQUENCE: 12
gtgcacccac ttaccc                                                     16

<210> SEQ ID NO 13
<211> LENGTH: 1401
<212> TYPE: DNA
<213> ORGANISM: Homo sapiens

<400> SEQUENCE: 13
atggttcact ccagcatggg ggctccagaa ataagaatgt ctaagcccct ggaggccgag      60
aagcaaggtc tggactcccc atcagagcac acagacaccg aaagaaatgg accagacact     120
aatcatcaga acccccaaaa taagacctcc ccattctccg tgtccccaac tggccccagt     180
acaaagatca aggctgaaga ccccagtggc gattcagccc agcagcaccc ctgccccct      240 cagccggccc agcctcatct gccccaggcc caactcatgt tgacgggcag ccagctagct     300
ggggacatac agcagctcct ccagctccag cagctggtgc ttgtgccagg ccaccacctc     360
cagccacctg ctcagttcct gctaccgcag gcccagcaga gccagccagg cctgctaccg     420
acaccaaatc tattccagct acctcagcaa acccagggag ctcttctgac ctcccagccc     480
cgggccgggc ttcccacaca ggccgtgacc cgccctacgc tgcccgaccc gcacctctcg     540
cacccgcagc ccccaaatg cttggagcca ccatcccacc ccgaggagcc cagtgatctg     600
gaggagctgg agcaattcgc ccgcaccttc aagcaacgcc gcatcaagct gggcttcacg     660
cagggtgatg tgggcctggc catgggcaag ctctacggca acgacttcag ccagacgacc     720
atttcccgct cgaggccct caacctgagc ttcaagaaca tgtgcaaact caagccctc     780 ctggagaagt ggctcaacga tgcagagact atgtctgtgg actcaagcct gcccagcccc     840
aaccagctga gcagccccag cctgggtttc gacggcctgc ccggccggag acgcaagaag     900
aggaccagca tcgagacaaa cgtccgcttc gccttagaga gagtttttct agcgaaccag     960

```
                                                            -continued
aagcctacct cagaggagat cctgctgatc gccgagcagc tgcacatgga gaaggaagtg      1020
atccgcgtct ggttctgcaa ccggcgccag aaggagaaac gcatcaaccc ctgcagtgcg      1080
gcccccatgc tgcccagccc agggaagccg gccagctaca gccccatat ggtcacaccc       1140 caaggggcg cggggacctt accgttgtcc aagcttcca gcagtctgag cacaacagtt        1200
actaccttat cctcagctgt ggggacgctc caccccagcc ggacagctgg aggggtggg       1260 ggcggggcg gggctgcgcc ccccctcaat tccatcccct ctgtcactcc ccaccccccg       1320
gccaccacca acagcacaaa ccccagccct caaggcagcc actcggctat cggcttgtca     1380
ggcctgaacc ccagcacggg g                                                1401

<210> SEQ ID NO 14
<211> LENGTH: 467
<212> TYPE: PRT
<213> ORGANISM: Homo sapiens

<400> SEQUENCE: 14

Met Val His Ser Ser Met Gly Ala Pro Glu Ile Arg Met Ser Lys Pro
1               5                   10                  15

Leu Glu Ala Glu Lys Gln Gly Leu Asp Ser Pro Ser Glu His Thr Asp
            20                  25                  30

Thr Glu Arg Asn Gly Pro Asp Thr Asn His Gln Asn Pro Gln Asn Lys
        35                  40                  45

Thr Ser Pro Phe Ser Val Ser Pro Thr Gly Pro Ser Thr Lys Ile Lys
    50                  55                  60

Ala Glu Asp Pro Ser Gly Asp Ser Ala Pro Ala Ala Pro Leu Pro Pro
65                  70                  75                  80

Gln Pro Ala Gln Pro His Leu Pro Gln Ala Gln Leu Met Leu Thr Gly
                85                  90                  95

Ser Gln Leu Ala Gly Asp Ile Gln Gln Leu Leu Gln Leu Gln Gln Leu
            100                 105                 110

Val Leu Val Pro Gly His His Leu Gln Pro Pro Ala Gln Phe Leu Leu
        115                 120                 125

Pro Gln Ala Gln Gln Ser Gln Pro Gly Leu Leu Pro Thr Pro Asn Leu
    130                 135                 140

Phe Gln Leu Pro Gln Gln Thr Gln Gly Ala Leu Leu Thr Ser Gln Pro
145                 150                 155                 160

Arg Ala Gly Leu Pro Thr Gln Ala Val Thr Arg Pro Thr Leu Pro Asp
                165                 170                 175

Pro His Leu Ser His Pro Gln Pro Pro Lys Cys Leu Glu Pro Pro Ser
            180                 185                 190

His Pro Glu Glu Pro Ser Asp Leu Glu Glu Leu Glu Gln Phe Ala Arg
        195                 200                 205

Thr Phe Lys Gln Arg Arg Ile Lys Leu Gly Phe Thr Gln Gly Asp Val
    210                 215                 220

Gly Leu Ala Met Gly Lys Leu Tyr Gly Asn Asp Phe Ser Gln Thr Thr
225                 230                 235                 240

Ile Ser Arg Phe Glu Ala Leu Asn Leu Ser Phe Lys Asn Met Cys Lys
                245                 250                 255

Leu Lys Pro Leu Leu Glu Lys Trp Leu Asn Asp Ala Glu Thr Met Ser
            260                 265                 270

Val Asp Ser Ser Leu Pro Ser Pro Asn Gln Leu Ser Ser Pro Ser Leu
        275                 280                 285

Gly Phe Asp Gly Leu Pro Gly Arg Arg Arg Lys Lys Arg Thr Ser Ile
```

-continued

```
                290                 295                 300
Glu Thr Asn Val Arg Phe Ala Leu Glu Lys Ser Phe Leu Ala Asn Gln
305                 310                 315                 320

Lys Pro Thr Ser Glu Glu Ile Leu Leu Ile Ala Glu Gln Leu His Met
                325                 330                 335

Glu Lys Glu Val Ile Arg Val Trp Phe Cys Asn Arg Arg Gln Lys Glu
            340                 345                 350

Lys Arg Ile Asn Pro Cys Ser Ala Ala Pro Met Leu Pro Ser Pro Gly
        355                 360                 365

Lys Pro Ala Ser Tyr Ser Pro His Met Val Thr Pro Gln Gly Gly Ala
    370                 375                 380

Gly Thr Leu Pro Leu Ser Gln Ala Ser Ser Ser Leu Ser Thr Thr Val
385                 390                 395                 400

Thr Thr Leu Ser Ser Ala Val Gly Thr Leu His Pro Ser Arg Thr Ala
                405                 410                 415

Gly Gly Gly Gly Gly Gly Gly Ala Ala Pro Pro Leu Asn Ser Ile
                420                 425                 430

Pro Ser Val Thr Pro Pro Pro Ala Thr Thr Asn Ser Thr Asn Pro
            435                 440                 445

Ser Pro Gln Gly Ser His Ser Ala Ile Gly Leu Ser Gly Leu Asn Pro
    450                 455                 460

Ser Thr Gly
465
```

```
<210> SEQ ID NO 15
<211> LENGTH: 10
<212> TYPE: DNA
<213> ORGANISM: Artificial Sequence
<220> FEATURE:
<221> NAME/KEY: unsure
<222> LOCATION: (2)
<223> OTHER INFORMATION: Consensus "octamer" DNA sequence bound by OCT-2
      peptide chains.  N is any nucleic acid.

<400> SEQUENCE: 15 tnatttgcat                                                            10

<210> SEQ ID NO 16
<211> LENGTH: 5
<212> TYPE: PRT
<213> ORGANISM: Artificial Sequence
<220> FEATURE:
<223> OTHER INFORMATION: Five carboxy terminal residues of OCT-2 variant
      peptide chain.

<400> SEQUENCE: 16

Asn Pro Ser Thr Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Five carboxy terminal residues of OCT-2 variant
      peptide chain.

<400> SEQUENCE: 17

Asn Pro Ser Ala Gly
1               5
```

-continued

```
<210> SEQ ID NO 18
<211> LENGTH: 5
<212> TYPE: PRT
<213> ORGANISM: Artificial Sequence
<220> FEATURE:
<221> NAME/KEY: unsure
<222> LOCATION: (4)
<223> OTHER INFORMATION: Five carboxy terminal residues of OCT-2 variant
      peptide chain where Xaa can be any one of the
      twenty naturally occurring amino acids

<400> SEQUENCE: 18

Asn Pro Ser Xaa Gly
1               5

<210> SEQ ID NO 19
<211> LENGTH: 12
<212> TYPE: PRT
<213> ORGANISM: Artificial Sequence
<220> FEATURE:
<223> OTHER INFORMATION: Twelve carboxy terminal residues of Homo
      sapiens wild-type/archetypal OCT-2 peptide chain.

<400> SEQUENCE: 19

Pro Gly Leu Trp Trp Asn Pro Ala Pro Tyr Gln Pro
1               5                   10
```

US 7,888,117 B2

HUMAN OCT-2 VARIANT PEPTIDE CHAINS, NUCLEIC ACIDS, AND METHODS

CROSS-REFERENCE TO RELATED APPLICATIONS

This application claims priority to U.S. Provisional Application No. 60/801,127, filed 17 May 2006, the entire contents of which is incorporated herein by reference.

FIELD OF THE INVENTION

The present invention relates to *Homo sapiens* OCT-2 variant peptide chains, polynucleotides encoding these peptide chains, cells comprising these polynucleotides, and methods of using the forgoing.

BACKGROUND OF THE INVENTION

Large-scale commercial production of proteins, such as antibodies, typically relies on expression of the protein by cultured eukaryotic cells. In general, it is recognized in the art that increasing mRNA copy number results in increased protein expression. Additionally, bioactive RNAs such as silencing RNAs (siRNA) are useful to prevent the expression of genes that produce undesired effects in cells. Large-scale production of proteins by cultured eukaryotic cells and bioactive RNA technologies are both dependent on the efficient transcription of genes into RNA encoding proteins or bioactive RNAs, respectively. However, low protein expression or low RNA transcript levels are common problems encountered in the use of these technologies.

The OCT-2 protein and its known homologs are transcription factors capable of increasing the production of RNA transcripts from genes responsive to this protein. The predominant, bioactive form of *Homo sapiens* OCT-2 (SEQ ID NO: 2) consists of 463 amino acid residues and contains an inhibitory domain, a DNA binding domain, and an activation domain (FIG. 1). The DNA binding domain of the OCT-2 protein binds the "octamer site" having the consensus sequence 5'-TNATTTGCAT-3' (SEQ ID NO: 15; where N is any nucleic acid residue) in the promoter or regulatory region of OCT-2 responsive genes. See Müller et al. in *Nature* 336: 544 (1988). After DNA binding, the activation domain of the OCT-2 protein is believed to interact with the *Homo sapiens* co-activator protein OBF-1 (SEQ ID NO: 8) to stabilize formation of an active RNA polymerase II protein complex that can produce RNA transcripts. See Boss, *Current Opin. In Immunol.* 9: 107 (1997). The activity of OCT-2 increases the rate of formation of active RNA polymerase II protein complexes resulting in an increase in the production of RNA transcripts from OCT-2 responsive genes.

Genes may be naturally OCT-2 responsive or engineered to become OCT-2 responsive by inserting an "octamer" DNA sequence into the promoter or regulatory region of the gene. Consequently, it is expected that low levels of protein expression or low bioactive RNA levels could be increased by overexpressing OCT-2 alone or with the OBF-1 coactivator protein to increase transcription of OCT-2 responsive genes. Thus, a need exists for novel OCT-2 compositions and effective methods for increasing the expression or transcription of OCT-2 responsive genes.

BRIEF DESCRIPTION OF THE DRAWINGS

FIG. 2. Multiple sequence alignment analysis of the wild-type, archetypical *Homo sapiens* OCT-2 protein (NP_002689; SEQ ID NO: 2); the *Homo sapiens* OCT-2 Clone #19 Variant Protein (Clone #19; SEQ ID NO: 6); the *Homo sapiens* OCT-2 Clone #38 Variant Protein (Clone#38; SEQ ID NO: 4); and the *Homo sapiens* OCT-2 protein predicted to be encoded by coding sequence 1 (CDS 1) of Accession M36653 (SEQ ID NO: 14).

SUMMARY OF THE INVENTION

Figure 1:
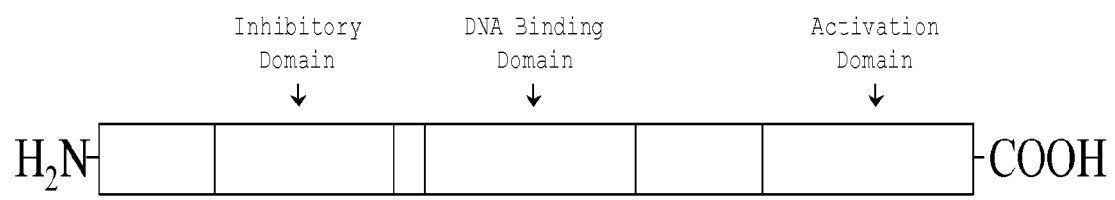
FIG. 1. Functional domains of a *Homo sapiens* OCT-2 peptide chain (SEQ ID NO: 2). Drawing is not to scale.

One aspect of the invention is an isolated nucleic acid comprising a nucleic acid having a sequence encoding a peptide chain having an amino acid sequence with at least 90% identity to amino acid residues 1 to 447 of SEQ ID NO: 6 wherein the five amino acid residues at the carboxy terminus of the peptide chain comprise the amino acid sequence Asparagine-Proline-Serine-Xaa-Glycine (SEQ ID NO: 18) where Xaa is any L-amino acid.

Another aspect of the invention is an isolated peptide chain having an amino acid sequence with at least 90% identity to amino acid residues 1 to 447 of SEQ ID NO: 6 wherein the five amino acid residues at the carboxy terminus of the peptide chain comprise the amino acid sequence Asparagine-Proline-Serine-Xaa-Glycine (SEQ ID NO: 18) where Xaa is any L-amino acid.

Another aspect of the invention is a method of increasing the expression of an OCT-2 responsive gene by a eukaryotic cell comprising the steps of providing a eukaryotic cell comprising an OCT-2 responsive gene; providing the eukaryotic cell with a first nucleic acid comprising a nucleic acid encoding a first peptide chain having an amino acid sequence with at least 90% identity to amino acid residues 1 to 447 of SEQ ID NO: 6 wherein the five amino acid residues at the carboxy terminus of the first peptide chain comprise the amino acid sequence Asparagine-Proline-Serine-Xaa-Glycine (SEQ ID NO: 18) where Xaa is any L-amino acid; and expressing the first peptide chain in the eukaryotic cell whereby the expression of the OCT-2 responsive gene is increased relative to a control eukaryotic cell that was not provided with the first nucleic acid.

Another aspect of the invention is a method of increasing the expression of an OCT-2 responsive gene by a eukaryotic cell comprising the steps of providing a eukaryotic cell comprising an OCT-2 responsive gene; providing the eukaryotic cell with a first nucleic acid comprising a nucleic acid encoding a first peptide chain comprising an amino acid sequence with at least 90% identity to amino acid residues 1 to 447 of SEQ ID NO: 6 wherein the five amino acid residues at the carboxy terminus of the peptide chain comprise the amino acid sequence Asparagine-Proline-Serine-Xaa-Glycine (SEQ ID NO: 18) where Xaa is any L-amino acid; providing the eukaryotic cell with a second nucleic acid encoding a second peptide chain having the amino acid sequence of SEQ ID NO: 10; and expressing the first peptide chain and the second peptide chain in the eukaryotic cell whereby the expression of the OCT-2 responsive gene is increased relative to a control eukaryotic cell that was not provided with the first and second nucleic acid.

Another aspect of the invention is a method of increasing the transcription of an OCT-2 responsive gene by a eukaryotic cell comprising the steps of providing a eukaryotic cell comprising an OCT-2 responsive gene; providing the eukaryotic cell with a first nucleic acid comprising a nucleic acid encoding a first peptide chain having an amino acid sequence with at least 90% identity to amino acid residues 1 to 447 of SEQ ID NO: 6 wherein the five amino acid residues at the carboxy terminus of the peptide chain comprise the amino acid sequence Asparagine-Proline-Serine-Xaa-Glycine (SEQ ID NO: 18) where Xaa is any L-amino acid; and expressing the first peptide chain in the eukaryotic cell whereby the transcription of the OCT-2 responsive gene is increased relative to a control eukaryotic cell that was not provided with the nucleic acid.

Another aspect of the invention is a method of increasing the transcription of an OCT-2 responsive gene by a eukaryotic cell comprising the steps of providing a eukaryotic cell comprising an OCT-2 responsive gene; providing the eukaryotic cell with a first nucleic acid comprising a nucleic acid encoding a first peptide chain having an amino acid sequence with at least 90% identity to amino acid residues 1 to 447 of SEQ ID NO: 6 wherein the five amino acid residues at the carboxy terminus of the peptide chain comprise the amino acid sequence Asparagine-Proline-Serine-Xaa-Glycine (SEQ ID NO: 18) where Xaa is any L-amino acid; providing the eukaryotic cell with a second nucleic acid encoding a second peptide chain having the amino acid sequence of SEQ ID NO: 10; and expressing the first peptide chain and the second peptide chain in the eukaryotic cell whereby the transcription of the OCT-2 responsive gene is increased relative to a control eukaryotic cell that was not provided with the first and second nucleic acid.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a cell" is a reference to one or more cells and includes equivalents thereof known to those skilled in the art.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the invention, exemplary compositions and methods are described herein.

The term "peptide chain" means a molecule that comprises at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "nucleic acid" means a molecule that comprises at least two nucleic acid residues linked to form a chain. Such nucleic acid residues may be those found in DNA or RNA.

The term "identity" means the percent identity between two aligned peptide chains. Identity between two peptide chains can be determined by pair-wise amino acid sequence alignment using the default settings of the AlignX module of Vector NTI v. 9.0.0 (Invitrogen Corp., Carslbad, Calif.). AlignX uses the CLUSTALW algorithm to perform pair-wise amino acid sequence alignments.

The term "eukaryotic cell" means a cell in which genetic material is organized into at least one membrane-bound nucleus.

The term "OCT-2 responsive gene" means a nucleic acid that encodes an RNA and responds to OCT-2 activity either directly through the binding of OCT-2 or an OCT-2 homolog to an octameric, consensus 5'-TNATTTGCAT-3' (SEQ ID NO: 15) OCT-2 DNA binding half-site or indirectly to OCT-2 activity. The RNA encoded by an OCT-2 responsive gene may be functional on its own as a small interfering RNA, silencing RNA, or ribozyme. The RNA encoded by an OCT-2 responsive gene may also be translated to produce a peptide chain.

The term "expressing" means the detectable production of a peptide chain encoded by a nucleic acid.

The term "myeloma cell" refers both to cancerous plasma cells obtained, or derived, from an organism with multiple myeloma and to hybridoma cells formed from the fusion of such a cancerous plasma cell with another cell (e.g. an antibody producing BALB/c mouse spleen cell or eukaryotic cell stably transfected with a nucleic acid encoding an antibody).

One aspect of the present invention is an isolated nucleic acid comprising a nucleic acid encoding a peptide chain comprising an amino acid sequence with at least 90% identity to amino acid residues 1 to 447 of SEQ ID NO: 6 wherein the five amino acid residues at the carboxy terminus of the peptide chain have the amino acid sequence Asparagine-Proline-Serine-Xaa-Glycine (SEQ ID NO: 18) where Xaa is any L-amino acid.

As those skilled in the art will recognize, the peptide chain encoded by the nucleic acid of the invention can be fused at its amino or carboxy termini to a second, heterologous peptide chain. Such heterologous peptide chains may be tags, domains, amino acid linker sequences or other peptide chain types. Examples of peptide chain tags include hexahistidine, flu antigen, and Fc domains. Peptide chain domains may include, for example, transcription activation domains and catalytically active domains such as peroxidases or chloramphenical acetyl transferase as well as other discrete protein domains. Amino acid linker sequences may be sterically unconstrained peptide chains such as those peptide chains that contain multiple glycine, serine, or proline amino acid residues. Those skilled in the art will recognize standard techniques for generating nucleic acids encoding heterologous protein fusions.

Levorotatory-amino acid (L-amino acid) residues include the twenty naturally occurring L-amino acids and naturally occurring post-translational modifications of these L-amino acids such as, for example, selenocysteine and pyrrolysine.

In one embodiment of the isolated nucleic acid of the invention the five amino acid residues at the carboxy terminus of the peptide chain have the sequence shown in SEQ ID NO: 16 or SEQ ID NO: 17.

In another embodiment the isolated nucleic acid of the invention comprises a nucleic acid sequence encoding SEQ ID NO: 4. SEQ ID NO: 4 is the amino acid sequence of the *Homo sapiens* OCT-2 Clone #38 variant peptide chain. An exemplary nucleic acid sequence encoding the amino acid sequence of SEQ ID NO: 4 is shown in SEQ ID NO: 3.

In another embodiment the isolated nucleic acid of the invention comprises a nucleic acid sequence encoding SEQ ID NO: 6. SEQ ID NO: 6 is the amino acid sequence of the *Homo sapiens* OCT-2 Clone #19 variant peptide chain. An exemplary nucleic acid sequence encoding the amino acid sequence of SEQ ID NO: 6 is shown in SEQ ID NO: 5.

Another embodiment of the invention is a cell comprising an isolated nucleic acid of the invention. Such a cell may be a prokaryotic, eukaryotic, or archaeal cell. It is preferred that such cells be suitable for the expression of peptide chains from the isolated nucleic acids of the invention or for the propagation of the isolated nucleic acids of the invention.

Another aspect of the invention is an isolated peptide chain comprising an amino acid sequence with at least 90% identity to amino acid residues 1 to 447 of SEQ ID NO: 6 wherein the five amino acid residues at the carboxy terminus of the peptide chain have the amino acid sequence Asparagine-Proline-Serine-Xaa-Glycine (SEQ ID NO: 18) where Xaa is any L-amino acid. As those skilled in the art will recognize, the peptide chain of the invention can be fused to a second, heterologous peptide chain. Such peptide chain fusions can be generated using standard molecular biology techniques to generate amino or carboxy terminal fusions. Alternatively, such peptide chain fusions can be generated by in vitro chemical coupling techniques to fuse peptide chains and generate amino terminal fusions, carboxy terminal fusions, or amino acid side chain fusions.

In another embodiment of the isolated peptide chain of the invention the five amino acid residues at the carboxy terminus of the peptide chain have the amino acid sequence shown in SEQ ID NO: 16 or SEQ ID NO: 17.

In another embodiment the isolated peptide chain of the invention has the amino acid sequence shown in SEQ ID NO: 4.

In another embodiment the isolated peptide chain of the invention has the amino acid sequence shown in SEQ ID NO: 6.

Another aspect of the invention is a method of increasing the expression of an OCT-2 responsive gene by a eukaryotic cell comprising the steps of providing a eukaryotic cell comprising an OCT-2 responsive gene; providing the eukaryotic cell with a first nucleic acid encoding a first peptide chain having an amino acid sequence with at least 90% identity to amino acid residues 1 to 447 of SEQ ID NO: 6 wherein the five amino acid residues at the carboxy terminus of the first peptide chain have the amino acid sequence Asparagine-Proline-Serine-Xaa-Glycine (SEQ ID NO: 18) where Xaa is any L-amino acid; and expressing the first peptide chain encoded by the first nucleic acid in the eukaryotic cell whereby the expression of the OCT-2 responsive gene is increased relative to a control eukaryotic cell that was not provided with the first nucleic acid.

Eukaryotic cells useful in the method of the invention include mammalian derived cells such as Chinese Hamster Ovary (CHO) cells, and myeloma cells such as SP2/0 cells (American Type Culture Collection (ATCC), Manasas, Va., CRL-1581) and C463A cells. C463A cells and the generation of C463A cells are described in US20030166146A1, which is herein incorporated by reference in its entirety. Such eukaryotic cells may be adapted for growth in chemically defined media lacking animal serum.

The term "OCT-2 responsive gene" is defined above. The RNA encoded by an OCT-2 responsive gene may be functional on its own as a small interfering RNA, silencing RNA, or ribozyme. The RNA encoded by an OCT-2 responsive gene may also be translated to produce a peptide chain. Such peptide chains may be antibody chains, fragments of antibody chains, catalytically active peptide chains, receptor agonist peptide chains, receptor antagonist peptide chains, and other peptide chains with any function that is desirable to express in an cell.

A eukaryotic cell comprises an OCT-2 responsive gene if such a gene is present in the cell. OCT-2 responsive genes may be native genes that have been modified by site specific or random recombination to be OCT-2 responsive genes that are naturally OCT-2 responsive. A native gene can be made OCT-2 responsive by introducing a nucleic acid containing an OCT-2 binding site into the promoter or regulatory region of the native gene. Alternatively, a gene can be made indirectly OCT-2 responsive by introducing a nucleic acid containing a promoter or regulatory region responsive to a transcriptional activator produced as a result of OCT-2 activity. An exogenous OCT-2 responsive gene can also be introduced into a eukaryotic cell. Such an exogenous OCT-2 responsive gene may be, for example, an antibody light or heavy chain gene construct under the control of an OCT-2 responsive promoter such as an immunoglobulin promoter. Site specific, targed recombination can also be used to place an exogenous gene under the control of an endogenous OCT-2 responsive regulatory region or promoter. Standard molecular biology, recombinant gene technology techniques and cell culture techniques well known to those skilled in the art can be used for the construction of OCT-2 responsive genes either in vitro or in vivo and for the identification of eukaryotic cells comprising an OCT-2 responsive gene.

A nucleic acid may be provided to eukaryotic cells in the method of the invention by well-known techniques such as cell fusion, electroporation, lipofection, viral infection, and calcium phosphate precipitation based techniques. Those skilled in the art will recognize other techniques for providing a nucleic acid to a eukaryotic cell.

Expression of an OCT-2 responsive gene is increased relative to a control eukaryotic cell when the level or activity of the peptide chain encoded by the OCT-2 responsive gene is increased relative to the control eukaryotic cell. Peptide chain levels may be measured by any means known in the art such as, for example, SDS-PAGE. Peptide chain activity levels can be measured using activity assays specific to the activity of the peptide chain. For example, antibody peptide chain expression may be measured by SDS-PAGE, and the antigen binding activity of an antibody may be measured using standard ELISA techniques well known in the art. Peptide chain levels or activity may be numerically expressed using any appropriate units and normalized if necessary. Normalization can be accomplished by using the level of a second peptide chain, the number of cells in a sample, or on the basis of elapsed time, for example.

In one embodiment of the method of the invention the first five amino acid residues at the carboxy terminus of the first peptide chain have the sequence shown in SEQ ID NO: 16 or SEQ ID NO: 17.

In another embodiment of the method of the invention the first peptide chain has the amino acid sequence shown in SEQ ID NO: 4.

In another embodiment of the method of the invention the first peptide chain has the amino acid sequence shown in SEQ ID NO: 6.

In another embodiment of the method of the invention the eukaryotic cell is a myeloma cell. Examples of myeloma cell lines useful in the methods of the invention include the SP2/0, NSO (European Collection of Cell Cultures (ECACC), Salisbury, Wiltshire, UK, ECACC No. 85110503), FO (ATCC CRL-1646), and Ag653 (ATCC CRL-1580) cell lines which were obtained from mice. An example of a myeloma cell line obtained from humans and useful in the methods of the invention is the U266 cell line (ATTC CRL-TIB-196). The C463A myeloma cell line is also useful in the methods of the invention and is an example of an SP2/0 derived cell line capable of growing in chemically defined media. Those skilled in the art will recognize other myeloma cell lines.

In another embodiment of the method of the invention the eukaryotic cell is selected from the group consisting of SP2/0, C463A, and CHO cells. Each of these cell types have the common properties of being suitable for in vitro culture and having the ability to express peptide chains at high levels.

Another aspect of the invention is a method of increasing the expression of an OCT-2 responsive gene by a eukaryotic cell comprising the steps of providing a eukaryotic cell comprising an OCT-2 responsive gene; providing the eukaryotic cell with a first nucleic acid encoding a first peptide chain having an amino acid sequence with at least 90% identity to amino acid residues 1 to 447 of SEQ ID NO: 6 wherein the five amino acid residues at the carboxy terminus of the peptide chain have the amino acid sequence Asparagine-Proline-Serine-Xaa-Glycine (SEQ ID NO: 18) where Xaa is any L-amino acid; providing the eukaryotic cell with a second nucleic acid encoding a second peptide chain having the amino acid sequence shown in SEQ ID NO: 8 or SEQ ID NO: 10; and expressing the first peptide chain and the second peptide chain in the eukaryotic cell whereby the expression of the OCT-2 responsive gene is increased relative to a control eukaryotic cell that was not provided with the first and second nucleic acid. SEQ ID NO 8 is the amino acid sequence of the Homo sapiens OBF-1 peptide chain. An exemplary nucleic acid sequence encoding the amino acid sequence of SEQ ID NO: 8 is shown in SEQ ID NO: 7. SEQ ID NO 10 is the amino acid sequence of the Mus musculus OBF-1 peptide chain. An exemplary nucleic acid sequence encoding the amino acid sequence of SEQ ID NO: 10 is shown in SEQ ID NO: 9.

In one embodiment of the method of the invention the first five amino acid residues at the carboxy terminus of the first peptide chain have the sequence shown in SEQ ID NO: 16 or SEQ ID NO: 17.

In another embodiment of the method of the invention, the OCT-2 responsive gene can be an antibody gene, such as a heavy or light chain gene.

In another embodiment of the method of the invention the first peptide chain has the amino acid sequence shown in SEQ ID NO: 4.

In another embodiment of the method of the invention the first peptide chain has the amino acid sequence shown in SEQ ID NO: 6.

In another embodiment of the method of the invention the eukaryotic cell is a myeloma cell.

In another embodiment of the method of the invention the eukaryotic cell is selected from the group consisting of SP2/0, C463A, and CHO cells.

Another aspect of the invention is a method of increasing the expression of an OCT-2 responsive antibody gene by an eukaryotic cell comprising the steps of providing a eukaryotic cell comprising an OCT-2 responsive antibody gene; providing the eukaryotic cell with a first nucleic acid encoding a first peptide chain having the sequence shown in SEQ ID NO: 4 or SEQ ID NO: 6; and expressing the first peptide chain encoded by the first nucleic acid in the eukaryotic cell whereby the expression of the OCT-2 responsive antibody gene is increased relative to a control eukaryotic cell that was not provided with the first nucleic acid.

In one embodiment of the method of the invention the eukaryotic cell is selected from the group consisting of SP2/0, C463A, and CHO cells.

Another aspect of the invention is a method of increasing the expression of an OCT-2 responsive antibody gene by a eukaryotic cell comprising the steps of providing a eukaryotic cell comprising an OCT-2 responsive gene; providing the eukaryotic cell with a first nucleic acid encoding a first peptide chain having the sequence shown in SEQ ID NO: 4 or SEQ ID NO: 6; providing the eukaryotic cell with a second nucleic acid encoding a second peptide chain having the amino sequence shown in SEQ ID NO: 10; and expressing the first peptide chain and the second peptide chain in the eukaryotic cell whereby the expression of the OCT-2 responsive antibody gene is increased relative to a control eukaryotic cell that was not provided with the first and second nucleic acid.

In one embodiment of the method of the invention the eukaryotic cell is selected from the group consisting of SP2/0, C463A, and CHO cells.

Another aspect of the invention is a method of increasing the transcription of an OCT-2 responsive gene by a eukaryotic cell comprising the steps of providing a eukaryotic cell comprising an OCT-2 responsive gene; providing the eukaryotic cell with a first nucleic acid comprising a nucleic acid encoding a first peptide chain having an amino acid sequence with at least 90% identity to amino acid residues 1 to 447 of SEQ ID NO: 6 wherein the five amino acid residues at the carboxy terminus of the peptide chain have the amino acid sequence Asparagine-Proline-Serine-Xaa-Glycine (SEQ ID NO: 18) where Xaa is any L-amino acid; and expressing the first peptide in the eukaryotic cell whereby the transcription of the OCT-2 responsive gene is increased relative to a control eukaryotic cell that was not provided with the nucleic acid.

Transcription of an OCT-2 responsive gene is increased relative to a control eukaryotic cell when the level or activity of the RNA transcript encoded by the OCT-2 responsive gene is increased relative to the control eukaryotic cell. RNA transcript levels may be measured by any means known in the art such as, for example RT-PCR and Northern blots. RNA transcript activity levels can be measured using ribozyme activity assays, silencing RNA assays, or antisense-RNA assays specific to the activity of the RNA transcript for example. RNA transcript levels or activity may be numerically expressed using any appropriate units and normalized if necessary. Normalization can be accomplished by using the level of a second RNA transcript, the number of cells in a sample, or on the basis of elapsed time, for example.

Another aspect of the invention is a method of increasing the transcription of an OCT-2 responsive gene by a eukaryotic cell comprising the steps of providing a eukaryotic cell comprising an OCT-2 responsive gene; providing the eukaryotic cell with a first nucleic acid comprising a nucleic acid encoding a first peptide chain having an amino acid sequence with at least 90% identity to amino acid residues 1 to 447 of SEQ ID NO: 6 wherein the five amino acid residues at the carboxy terminus of the peptide chain have the amino acid sequence Asparagine-Proline-Serine-Xaa-Glycine (SEQ ID NO: 18) where Xaa is any L-amino acid; providing the eukaryotic cell with a second nucleic acid encoding a second peptide chain having the amino acid sequence of SEQ ID NO: 10; and expressing the first peptide chain and the second peptide chain in the eukaryotic cell whereby the transcription of the OCT-2 responsive gene is increased relative to a control eukaryotic cell that was not provided with the first and second nucleic acid.

The present invention is further described with reference to the following examples. These examples are merely to illustrate aspects of the present invention and are not intended as limitations of this invention.

EXAMPLE 1

Isolation of cDNA Encoding *Homo sapiens* OCT-2 Variant Proteins

Two cDNAs encoding the *Homo sapiens* OCT-2 Clone #38 (SEQ ID NO: 4) and *Homo sapiens* OCT-2 Clone #19 (SEQ ID NO: 6) variant proteins were isolated and sequenced. The cDNA (SEQ ID NO: 3) encoding the *Homo sapiens* OCT-2 Clone #38 variant protein (SEQ ID NO: 4) and the cDNA (SEQ ID NO: 5) encoding the *Homo sapiens* OCT-2 Clone #19 variant protein (SEQ ID NO: 6) were isolated using standard polymerase chain reaction (PCR) techniques from a *Homo sapiens* cDNA library (Stratagene Inc., La Jolla, Calif.).

The nucleic acid sequences of the forward primer and reverse primer used in the PCR amplification of SEQ ID NO: 4 and SEQ ID NO: 6 encoding these *Homo sapiens* OCT-2 protein variants are shown in SEQ ID NO: 11 (forward primer) and SEQ ID NO: 12 (reverse primer). These primers were designed using the nucleic acid sequence described in Accession M36653. Accession M36653 contains two open reading frames, designated CDS 1 and CDS 2, and encodes a *Homo sapiens* OCT-2 protein. This *Homo sapiens* OCT-2 protein is predicted to be encoded by CDS 1. The forward (SEQ ID NO: 11) and reverse (SEQ ID NO: 12) primers are specific to the 5' untranslated region (UTRs) flanking CDS 1 in Accession M36653 and a sequence located 3' to CDS 1 of the nucleic acid sequence described by Accession M36653. PCR using these primers amplifies any library nucleic acid sequences located between the binding sites of these two primers. Amplified DNA fragments resulting from PCR using these primers were isolated, cloned into the pCDNA3.1 expression vector (Invitrogen Inc., Carlsbad, Calif.), and sequenced using standard molecular biology techniques.

Sequencing, conceptual translations, and multiple sequence alignment analysis (FIG. 2) revealed that two unique nucleic acid sequences encoding the *Homo sapiens* OCT-2 Clone #38 protein and *Homo sapiens* OCT-2 Clone #19 protein had been isolated. This analysis showed these two clones encoded *Homo sapiens* OCT-2 variant proteins that are different than the wild-type, archetypical *Homo sapiens* OCT-2 protein (SEQ ID NO: 1) described by Accession NP-002689 and the *Homo sapiens* OCT-2 protein (SEQ ID NO: 14) predicted to be encoded by CDS 1 (SEQ ID NO: 13) of Accession M36653. As seen in the multiple protein sequence alignments of FIG. 2 the *Homo sapiens* OCT-2 Clone #38 protein sequence (SEQ ID NO: 4) and *Homo sapiens* OCT-2 Clone #19 protein sequence (SEQ ID NO: 6) both lack twelve carboxy-terminal amino acid residues (SEQ ID NO: 19) found in the wild-type, archetypal *Homo sapiens* OCT-2 protein sequence described by Accession NP_002689 (SEQ ID NO: 2). Further, as seen in the multiple protein sequence alignments of FIG. 2 the *Homo sapiens* OCT-2 Clone #38 protein sequence (SEQ ID NO: 4) and *Homo sapiens* OCT-2 Clone #19 protein sequence (SEQ ID NO: 6) both lack an 11 amino acid residue sequence found at position 166 to 181 of the *Homo sapiens* OCT-2 protein predicted to be encoded by CDS 1 of Accession M36653 (SEQ ID NO: 14). Lastly, multiple protein sequence alignment (FIG. 2) also revealed that the *Homo sapiens* OCT-2 Clone #19 protein sequence (SEQ ID NO: 6) has an serine (S) amino acid residue at position 116, instead of the proline (P) residue found at position 116 in the wild-type, archetypical *Homo sapiens* OCT-2 (SEQ ID NO: 2), Clone #38 protein sequences (SEQ ID NO: 4), and the *Homo sapiens* OCT-2 protein predicted to be encoded by CDS 1 of Accession M36653 (SEQ ID NO: 14). Multiple sequence alignment analysis was performed using the CLUSTALW algorithm and the CLUSTALW default settings. These results demonstrate that two new *Homo sapiens* OCT-2 protein variants had been isolated and identified.

EXAMPLE 2

Overexpression of OCT-2 Variant Protein and OBF-1 Increases Antibody Gene Transcript and Expression Levels Stable overexpression of *Homo sapiens* OCT-2 Clone #38 variant protein alone (SEQ ID NO: 4), and in combination with overexpression of Mus musculus OBF-1 (SEQ ID NO: 10) increased recombinant antibody heavy and light chain gene transcript (FIG. 3) and expression levels (FIG. 4) in C463A cells.

Control C463A cells for this experiment were stably cotransfected using standard methods, with a heavy chain expression vector and a light chain expression vector. OCT-2 transfected cells were stably cotransfected with the heavy chain expression vector, the light chain expression vector, and a pcDNA3.1/hOCT-2 vector encoding *Homo sapiens* OCT-2 Clone #38 (SEQ ID NO: 4). OCT-2 and OBF-1 transfected cells were stably contransfected with the heavy chain expression vector, the light chain expression vector, pcDNA3.1/hOCT-2 and pcDNA3.1/mOBF-1 vector encoding *Mus musculus* OBF-1 (SEQ ID NO: 10).

C463A cells were derived from Mus musculus SP2/0 myeloma cells and were adapted for growth in chemically defined culture medium. The heavy and light chain expression vectors encode the heavy and light chains of a fully human, tumor necrosis factor-alpha (TNF-alpha) specific, monoclonal antibody. An immunoglobulin promoter driving heavy and light chain expression by the heavy chain expression vector and the light chain expression vectors contains an octameric, consensus (5'-TNATTTGCAT-3'; SEQ ID NO: 15) OCT-2 DNA binding half-site. This OCT-2 DNA site makes heavy and light chain gene transcription from the heavy chain expression vector and the light chain expression vector responsive to OCT-2 activity. The heavy chain expression vector, light chain expression vector, pcDNA3.1/hOCT-2 and pcDNA3.1/mOBF-1 vectors each constitutively express the various proteins they encode.

Transfections were performed by electroporation of approximately $1 \times 10^7$ C463A cells using standard methods. Control C463A cells were stably transfected by electroporation with 4 µg of heavy chain expression vector, 4 µg light chain expression vector, and 2 µg pcDNA3.1. OCT-2 C463A cells were stably transfected with 4 µg of heavy chain expression vector, 4 µg of light chain expression vector, and 2 µg pcDNA3.1/hOCT-2. OCT-2 C463A cells were stably transfected with 4 µg of heavy chain expression vector, 4 µg of light chain expression vector, 2 µg pcDNA3.1/hOCT-2 and 2 µg pcDNA3.1/mOBF-1. MHX (mycophenolic acid, hypoxanthine, and xanthine) and standard methods were used to select cells stably transfected with the heavy chain expression vector and light chain expression vector. G418 and standard methods were used to select cells stably transfected with pcDNA3.1/hOCT-2 and pcDNA3.1/mOBF-1 cells. ELISA assays were then performed using standard methods to identify clones with the highest expression of the fully human, recombinant, tumor necrosis factor-alpha (TNF-alpha) specific, monoclonal antibody encoded by the heavy chain expression vector and light chain expression vector (FIG. 4).

Figure 3:
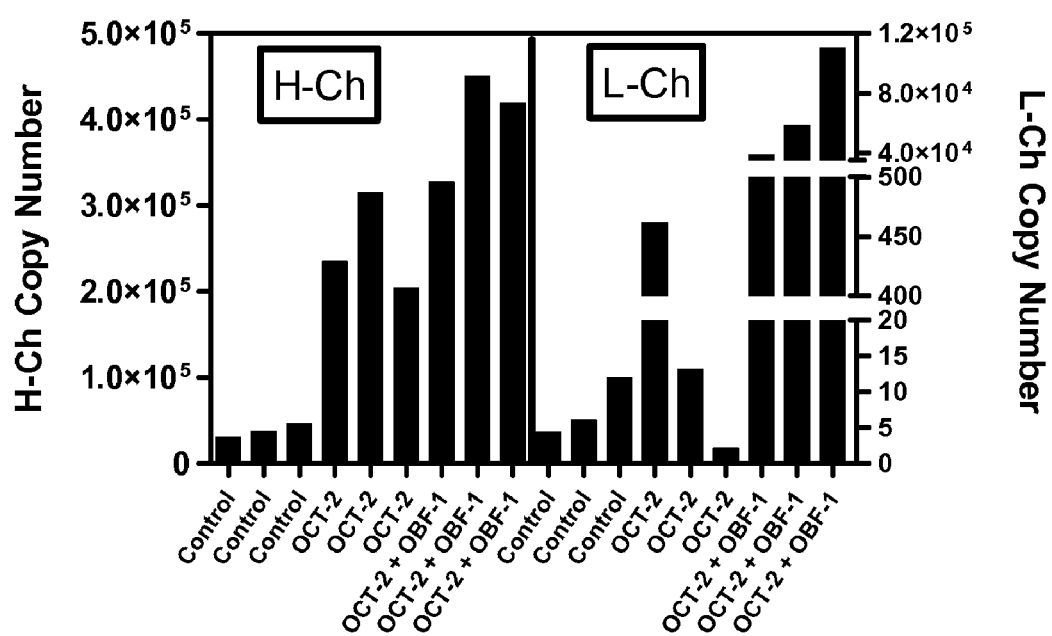
FIG. 3. Overexpression of *Homo sapiens* OCT-2 Clone #38 Variant Protein (SEQ ID NO: 4) alone and in combination with the *Mus musculus* OBF-1 protein (SEQ ID NO: 10) increases OCT-2 responsive antibody heavy and light chain gene transcript levels in eukaryotic C463A cells.
Figure 4:
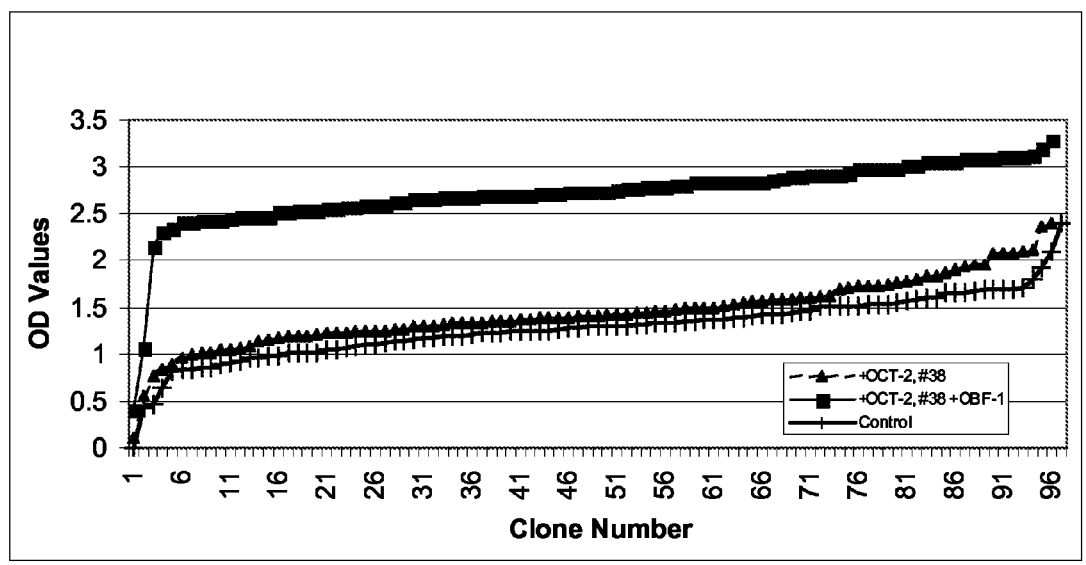
FIG. 4. Overexpression of *Homo sapiens* OCT-2 Clone #38 Variant Protein (SEQ ID NO: 4) alone and in combination with the *Mus musculus* OBF-1 protein (SEQ ID NO: 10) increases OCT-2 responsive antibody gene expression levels in eukaryotic C463A cells.

Stable expression of the *Homo sapiens* OCT-2 Clone #38 variant protein alone increased recombinant antibody gene transcript and expression levels relative to control cells (FIG. 3 and FIG. 4). Stable co-expression of the *Homo sapiens* OCT-2 Clone #38 (SEQ ID NO: 4) variant protein and Mus musculus OBF-1 protein (SEQ ID NO: 10) further increased recombinant antibody expression relative to control cells and cells expressing OCT-2 Clone #38 variant protein (SEQ ID NO: 4) alone (FIG. 3 and FIG. 4). Together these results indicate that the *Homo sapiens* OCT-2 Clone #38 variant protein is biologically active, capable of binding OCT-2 DNA binding sites to enhance gene activation and is capable of interacting with the Mus musculus OBF-1 protein to activate OCT-2 responsive gene expression.

The present invention now being fully described, it will be apparent to one of ordinary skill in the art that many changes and modifications can be made thereto without departing from the spirit or scope of the appended claims.

The invention claimed is:

1. An isolated nucleic acid comprising a nucleic acid encoding a peptide chain comprising the amino acid sequence as shown in residues 1 to 447 of SEQ ID NO: 4 or 6 wherein the five amino acid residues at the carboxy terminus of the peptide chain have the amino acid sequence Asparagine-Proline-Serine-Xaa-Glycine (SEQ ID NO: 18) where Xaa is any L-amino acid.

2. The isolated nucleic acid of claim 1 wherein the five amino acid residues at the carboxy terminus of the peptide chain have the sequence shown in SEQ ID NO: 16 or SEQ ID NO: 17.

3. The isolated nucleic acid of claim 2 encoding a peptide chain having the amino acid sequence shown in SEQ ID NO: 4.

4. The isolated nucleic acid of claim 2 encoding a peptide chain having the amino acid sequence shown in SEQ ID NO: 6.

5. An isolated host cell transformed or transfected with the isolated nucleic acid of claim 1, 2, 3 or 4.

6. An isolated peptide chain comprising the amino acid sequence as shown in residues 1 to 447 of SEQ ID NO: 4 or 6 wherein the five amino acid residues at the carboxy terminus of the peptide chain have the amino acid sequence Asparagine-Proline-Serine-Xaa-Glycine (SEQ ID NO: 18) where Xaa is any L-amino acid.

7. The isolated peptide chain of claim 6 where the five amino acid residues at the carboxy terminus of the peptide chain have the sequence shown in SEQ ID NO: 16 or SEQ ID NO: 17.

8. The isolated peptide chain of claim 7 having the amino acid sequence shown in SEQ ID NO: 4.

9. The isolated peptide chain of claim 7 having the amino acid sequence shown in SEQ ID NO: 6.

* * * * *